United States Patent
Vind et al.

(10) Patent No.: US 9,273,320 B2
(45) Date of Patent: Mar. 1, 2016

(54) METHOD OF PRODUCING A SWEET PROTEIN

(75) Inventors: Jesper Vind, Vaerloese (DK); Jeppe Wegener Tams, Gentofe (DK); Lars Beier, Lyngby (DK); Carsten Lillelund Olsen, Bagsvaerd (DK)

(73) Assignee: NOVOZYMES A/S, Bagsvaerd (DK)

( * ) Notice: Subject to any disclaimer, the term of this patent is extended or adjusted under 35 U.S.C. 154(b) by 647 days.

(21) Appl. No.: 13/382,535

(22) PCT Filed: Aug. 5, 2010

(86) PCT No.: PCT/EP2010/061435
§ 371 (c)(1),
(2), (4) Date: Jan. 6, 2012

(87) PCT Pub. No.: WO2011/015633
PCT Pub. Date: Feb. 10, 2011

(65) Prior Publication Data
US 2012/0107873 A1    May 3, 2012

Related U.S. Application Data

(60) Provisional application No. 61/232,141, filed on Aug. 7, 2009.

(30) Foreign Application Priority Data

Aug. 7, 2009   (EP) .................................... 09167464

(51) Int. Cl.
*C12N 15/80*   (2006.01)
*A23C 9/13*   (2006.01)
*A23L 1/236*   (2006.01)
*C07K 14/43*   (2006.01)

(52) U.S. Cl.
CPC .............. *C12N 15/80* (2013.01); *A23C 9/1307* (2013.01); *A23L 1/2361* (2013.01); *C07K 14/43* (2013.01)

(58) Field of Classification Search
None
See application file for complete search history.

(56) References Cited

U.S. PATENT DOCUMENTS

| 5,326,580 A | 7/1994 | Hellekant et al. |
| 2010/0076176 A1 | 3/2010 | Miles et al. |

FOREIGN PATENT DOCUMENTS

| WO | 95/31547 A1 | 11/1995 |
| WO | 2006/097464 A1 | 9/2006 |
| WO | 2008/112475 A2 | 9/2008 |
| WO | 2010/030999 A1 | 3/2010 |

OTHER PUBLICATIONS

Chris Bo, Synthesize the Plant Sweet Protein Brazzein Gene with Overlapping PCR, Biotechnology, Apr. 2007, Abstract, published on website: http://en.cnki.com.cn/Article_en/CJFDTOTAL-SWJS200704014.htm. Retrieved on Jul. 27, 2014.*
Hellekant et al., Chemical Senses, vol. 30, Suppl. 1, pp. i88-i89 (2005).
Moralejo et al., Applied and Environmental Microbiology, vol. 65, No. 3, pp. 1168-1174 (1999).
Assadi-Porter et al., Archives of Biochemistry and Biophysics, vol. 376, No. 2, pp. 252-258 (2000).
Berlec et al., Letters in Applied Microbiology, vol. 46, No. 2, pp. 227-231 (2008).
Faus, Appl. Microbiol. Biotech., vol. 53, No. 2, pp. 145-151 (2000).
Guan et al., Chemical Senses, vol. 20, No. 6, pp. 701 (1995), Abstract only.
Lamphear et al., Plant Biotechnology Journal, vol. 3, No. 1, pp. 103-114 (2005).
Lee et al., Biochemistry, vol. 27, pp. 5101-5107 (1988).
Masuda et al., Journal of Bioscience and Bioengineering, vol. 102, No. 5, pp. 375-389 (2006).
Tamas et al., Journal of Cereal Science, vol. 43, pp. 259-274 (2006).
Van Den Hombergh et al., Tibtech, vol. 15, No. 7, pp. 256-263 (1997).
Chen Bo et al, Biotechnology, vol. 17, No. 4, pp. 43-47 (2007). Abstract Only

* cited by examiner

*Primary Examiner* — Reza Ghafoorian
(74) *Attorney, Agent, or Firm* — Kristin McNamara

(57) ABSTRACT

The present invention relates to a method of producing a recombinant sweet protein in a filamentous fungus. The invention also relates to isolated polynucleotides encoding the sweet protein and to nucleic acid constructs, vectors, and host cells comprising the polynucleotides, as well as methods of using the sweet protein produced by the method of the invention.

14 Claims, No Drawings

SEQUENCE LISTING

```
<160> NUMBER OF SEQ ID NOS: 2

<210> SEQ ID NO 1
<211> LENGTH: 400
<212> TYPE: DNA
<213> ORGANISM: Artificial
<220> FEATURE:
<223> OTHER INFORMATION: Synthetic construct
<220> FEATURE:
<221> NAME/KEY: CDS
<222> LOCATION: (10)..(58)
<220> FEATURE:
<221> NAME/KEY: sig_peptide
<222> LOCATION: (10)..(58)
<220> FEATURE:
<221> NAME/KEY: Intron
<222> LOCATION: (59)..(113)
<220> FEATURE:
<221> NAME/KEY: CDS
<222> LOCATION: (114)..(391)
<220> FEATURE:
<221> NAME/KEY: sig_peptide
<222> LOCATION: (114)..(133)
<220> FEATURE:
<221> NAME/KEY: mat_peptide
<222> LOCATION: (230)..(391)

<400> SEQUENCE: 1 ggatccacc atg caa ttt acc acc atc ctc tcc atc ggt atc acc gtc ttc      51
          Met Gln Phe Thr Thr Ile Leu Ser Ile Gly Ile Thr Val Phe
          -55             -50                 -45 gga ctg g gtatgtacac caccccttg cgtctgatct gtgacatatg tagctgactg      108
Gly Leu
-40 gtcag cc  aac acc gga gcc ttt gca gca ccc cag ccg gta ccc gag gct    157
          Ala Asn Thr Gly Ala Phe Ala Ala Pro Gln Pro Val Pro Glu Ala
                      -35                 -30                 -25 tac gct gtt tct gat ccc gag gct cat cct gac gat ttt gct ggt atg      205
Tyr Ala Val Ser Asp Pro Glu Ala His Pro Asp Asp Phe Ala Gly Met
                -20                 -15                 -10 gat gcg aac caa ctt cag aaa cgt gaa gac aaa tgt aag aag gta tac      253
Asp Ala Asn Gln Leu Gln Lys Arg Glu Asp Lys Cys Lys Lys Val Tyr
            -5                  -1 1                 5 gag aac tac ccg gtc tcg aag tgc caa ttg gct aac cag tgc aac tac      301
Glu Asn Tyr Pro Val Ser Lys Cys Gln Leu Ala Asn Gln Cys Asn Tyr
        10                  15                  20 gac tgc aaa ttg gac aag cac gcg cgc tct ggc gag tgc ttc tac gac      349
Asp Cys Lys Leu Asp Lys His Ala Arg Ser Gly Glu Cys Phe Tyr Asp
25                  30                  35                  40
```

```
gag aag cgc aac cta cag tgc atc tgc gac tac tgc gaa tat tagctcgag      400
Glu Lys Arg Asn Leu Gln Cys Ile Cys Asp Tyr Cys Glu Tyr
                    45                  50
```

<210> SEQ ID NO 2
<211> LENGTH: 109
<212> TYPE: PRT
<213> ORGANISM: Artificial
<220> FEATURE:
<223> OTHER INFORMATION: Synthetic Construct

<400> SEQUENCE: 2

```
Met Gln Phe Thr Thr Ile Leu Ser Ile Gly Ile Thr Val Phe Gly Leu
-55             -50             -45             -40

Ala Asn Thr Gly Ala Phe Ala Ala Pro Gln Pro Val Pro Glu Ala Tyr
            -35             -30                 -25

Ala Val Ser Asp Pro Glu Ala His Pro Asp Asp Phe Ala Gly Met Asp
        -20             -15                 -10

Ala Asn Gln Leu Gln Lys Arg Glu Asp Lys Cys Lys Lys Val Tyr Glu
    -5              -1  1               5

Asn Tyr Pro Val Ser Lys Cys Gln Leu Ala Asn Gln Cys Asn Tyr Asp
10              15              20              25

Cys Lys Leu Asp Lys His Ala Arg Ser Gly Glu Cys Phe Tyr Asp Glu
            30              35              40

Lys Arg Asn Leu Gln Cys Ile Cys Asp Tyr Cys Glu Tyr
            45              50
```

METHOD OF PRODUCING A SWEET PROTEIN

CROSS-REFERENCE TO RELATED APPLICATIONS

This application is a 35 U.S.C. 371 national application of PCT/EP2010/061435 filed Aug. 5, 2010, which claims priority or the benefit under 35 U.S.C. 119 of European application no. 09167464.8 filed Aug. 7, 2009 and U.S. provisional application No. 61/232,141 filed Aug. 7, 2009, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a method of producing a recombinant sweet protein in a filamentous fungus. The invention also relates to isolated polynucleotides encoding the sweet protein and to nucleic acid constructs, vectors, and host cells comprising the polynucleotides, as well as methods of using the sweet protein produced by the method of the invention.

BACKGROUND OF THE INVENTION

Due to increasing attention to the negative health effects of obesity, a market demand for food and beverage products having alternative nutritional characteristics, including, for example, reduced calorie content, has increased as well. There is a market demand to replace the high-calorie sweeteners typically used in food and beverage products, such as sucrose and high fructose corn syrup (HFCS), with non-nutritive sweeteners. A number of such non-nutritive sweeteners have been identified. Some of these are small proteins which are naturally found in plants. Such proteins are often referred to as sweet proteins.

Brazzein is a sweet protein which can be extracted from the fruit of the West African climbing plant *Pentadiplandra brazzeana* Baillon (WO9531547). It has been characterized as a monomer protein having a 3-dimensional structure with four evenly spaced disulfide bonds. Three forms of the protein seem to exist in nature differing only at the N-terminal amino acid residue. One corresponds to the predicted 54-amino acid translation product containing a glutamine at its N-terminus. This form has been shown to be short lived as the N-terminal glutamine undergoes natural conversion to pyroglutamate, resulting in the second form. The loss of the N-terminal glutamine or pyroglutamate yields the 53-amino acid form which has been reported to be twice as sweet as the form having an N-terminal pyroglutamate (Lamphear, Barry J. et al. (2005) *Plant Biotechnology Journal* 3(1): 103-114).

On weight basis, brazzein is 500 to 2,000 times sweeter than sugar. Its sweet perception is quite similar to that of sucrose with a clean sweet taste with lingering aftertaste. Further, it has been shown to be stable over a broad pH range (2.5 to 8) and it can withstand heat which makes it suitable for many industrial food manufacturing processes. As a protein it is safe for diabetics and very soluble in water (>50 mg/ml). Brazzein thus represents a very good alternative to other available low calorie sweeteners.

Natural sourcing from *P. brazzeana* is difficult and expensive, though, and therefore alternatives for sourcing of the protein are being searched for. Brazzein can be chemically synthesised, which is useful for production of, e.g., variants in small scale, but not suitable for large scale production. Heterologous production in *E. coli* of brazzein or variants of brazzein has been described (see, e.g., Assadi-Porter, F. M. et al. (2000) *Arch. Biochem. Biophys.* 376(2): 252-258; WO2008112475). The bacterial system is ideal for structural investigations because it is easy to manipulate genetically and well suited for isotopic labelling. Expression of plant proteins from *E. coli* may be performed using the advantage of forming inclusion bodies inside the cell that can quite easily be separated from host proteins. However, proteins unfold and precipitate in inclusion bodies, and controlling correct S—S bond formation after resolubilization and refolding is not always easy (see, e.g., Tamás and Shewry (2006) *Journal of Cereal Science* 43: 259-274). Also, heterologous protein expression using inclusion bodies normally requires a number of purification steps which make such systems less suitable for industrial scale production.

Genetic engineering into plants, such as maize or wheat, has also been described. Brazzein-containing germ flour from maize has been demonstrated useful as a low-intensity sweetener providing a low-calorie alternative to sucrose, which also gives the intrinsic bulking properties necessary to replace the volume lost on removal of sugar. Also, a high-intensity sweetener based on corn-expressed brazzein could potentially be provided from enrichment of such material, which would extend the range of product applications (Lamphear, Barry J. et al. (2005) *Plant Biotechnology Journal* 3(1): 103-114).

Commercial-scale production of purified brazzein to be used as high-intensity sweetener may be more economic from a microbial system, though. But, in general, industrial production of plant proteins from microbial systems is not straightforward, and obtaining a correctly folded plant protein in high yield from a microorganism may be challenging and is not always possible. One factor which may complicate heterologous expression of brazzein from a microbial system is the small size of the protein. Another factor is the existence of numerous cysteine residues because of, e.g., the possibility of non-native S—S bond formation, possibly leading to loss of function or to intermolecular aggregation, e.g., during secretion. Thaumatin, which is another sweet protein originating from a plant, has been successfully expressed intracellularly in yeast in considerable quantities; however the yeast cells lacked the ability to process this molecule into a functional protein having sweet taste (Lee, J.-H. et al. (1988) *Biochemistry* 27: 5101-5107).

One purpose for the present inventors has been to identify a method for production of brazzein to be used as a high-intensity sweetener which can be performed in industrial scale. Industrial scale production at low cost requires that the protein is expressed in high yield and can easily be purified in a functionally folded 3-dimensional form possessing the same sweet phenotype as the natural product.

SUMMARY OF THE INVENTION

The present inventors have found a method for production of brazzein from a filamentous fungus which results in a secreted protein that can easily be separated from the host strain by removal of the biological material, e.g., by filtration resulting in a solution of quite pure brazzein protein. The protein can be expressed in high yield and no resolubilization or refolding is required as the brazzein obtained is apparently in its native form providing sweet taste. By applying such production method industrially, brazzein can be produced more cost-efficiently than previously disclosed methods of production.

The present invention therefore relates to a method of producing a recombinant sweet protein comprising an amino acid sequence having at least 70% identity to amino acids 2 to 54 of SEQ ID NO: 2, which comprises:
a) cultivating an *Aspergillus* host cell comprising a nucleic acid construct comprising a polynucleotide encoding the sweet protein under conditions conducive for production of the sweet protein; and
b) recovering the sweet protein.

The invention further relates to an isolated polynucleotide comprising a nucleotide sequence having at least 70% identity to nucleotide 233 to 391 of SEQ ID NO: 1 which encodes a sweet protein, to a nucleic acid construct comprising such polynucleotide, to a recombinant expression vector comprising such nucleic acid construct and to a recombinant *Aspergillus* host cell comprising such expression vector.

Brazzein protein obtained by above method was shown to be in a functional 3-dimensional form, i.e., a form providing sweet taste, when being recovered from the fermentation tank. Therefore, no refolding is required, i.e., a sweet protein obtained according to the present invention can be purified from the fermentation tank and applied directly as sweetening agent without any steps of denaturation by addition of reducing agent followed by oxidation under controlled conditions to ensure correct S—S bond formation. In a preferred aspect, the invention therefore relates to a method of producing a sweetening agent, which comprises:
a) cultivating an *Aspergillus* host cell comprising a polynucleotide sequence encoding a sweet protein comprising an amino acid sequence having at least 70% identity to amino acids 2 to 54 of SEQ ID NO: 2 under conditions conducive for production of the sweet protein;
b) recovering the sweet protein in a functional form as secreted from the host cell; and
c) applying the functional sweet protein as active ingredient in the sweetening agent.

The invention also relates to a method of increasing the sweetness of a food, beverage or medication product for human consumption comprising the step of adding a sufficient amount of a sweet protein to the product, so that the product has an increased sweetness, wherein the sweet protein has been produced according to a method as described above, and to a food, beverage or medication product for human consumption which comprises such sweet protein.

DEFINITIONS

Sweet protein: The term "sweet protein" as used herein refers to a protein having an intense sweet taste which is suitable for sweetening of food, beverage and/or medication products for human consumption. On weight basis, a sweet protein according to the present invention may be at least 100, preferably at least 200, more preferably at least 500, and even more preferably at least 1,000, times sweeter than sucrose, when compared to a 2% solution of sucrose. For purposes of the present invention, comparison of sweetness may be determined by testing human perception of sweetness of the protein against known controls using varied concentrations of the protein being diluted in water or in an aqueous solution which avoid adsorption on surfaces, such as 20% skim milk, e.g., as described in Example 3 of the present application.

The sweet proteins of the present invention may be at least 20%, preferably at least 40%, more preferably at least 50%, more preferably at least 60%, more preferably at least 70%, more preferably at least 80%, even more preferably at least 90%, most preferably at least 95%, and even most preferably at least 100%, as sweet as brazzein having the amino acid sequence shown as amino acids 2 to 54 of SEQ ID NO: 2 and being folded in its native 3-dimensional form.

Functional: The term "functional" sweet protein or "functional form" of a sweet protein as used herein refers to a form of the sweet protein where it is functionally folded in a 3-dimensional form which provides a sweet taste. Preferably, on weight basis, a functional sweet protein according to the present invention may be at least 100, preferably at least 200, more preferably at least 500, and even more preferably at least 1,000, times sweeter than sucrose, when compared to a 2% solution of sucrose. Preferably, a functional sweet protein according to the present invention is at least 20%, preferably at least 40%, more preferably at least 50%, more preferably at least 60%, more preferably at least 70%, more preferably at least 80%, even more preferably at least 90%, most preferably at least 95%, and even most preferably at least 100%, as sweet as brazzein having the amino acid sequence shown as amino acids 2 to 54 of SEQ ID NO: 2 and being folded in its native 3-dimensional form.

Sweetening agent: The term "sweetening agent" as used herein refers to a product or a composition which is in a form where it can be directly applied for sweetening of food, beverage and/or medication products for human consumption. The sweetening agent may comprise a single active ingredient, i.e., a single substance having a sweet taste, or it may comprise several of such active ingredients, i.e. a blend of substances contributing to the sweet taste. The sweetening agent may be the active ingredient(s) essentially in its (/their) pure form, e.g., a sweet protein which has been isolated from its production cells and is now in a form where it can be applied into a product intended for human consumption. Or the sweetening agent may comprise other substances in addition to the active ingredient(s), such as, e.g., fillers (e.g. lactose). The sweetening agent may be further blended with other substances before being applied into food or beverage products, or before being sold to end-consumers for household purposes, such as for sweetening of tea or coffee.

Active ingredient: The term "active ingredient" as used herein refers to the part of a product or a composition which actually does what the product or the composition is designed to do. I.e., an active ingredient in a sweetening agent is the substance, such as the sweet protein, which provides the sweet taste.

Brazzein: The term "brazzein" as used herein refers to the sweet protein which can be extracted from the fruit of the West African climbing plant *Pentadiplandra brazzeana* Baillon, and which is described in WO9531547, or a recombinantly produced form hereof. In nature, brazzein seems to appear in three alternative forms, with or without a Gln residue or a pyroglutamate attached to its N-terminus. In the context of the present invention, brazzein preferably comprises the amino acid sequence shown as amino acids 2 to 54 of SEQ ID NO: 2, more preferably it consists of the amino acid sequence shown as amino acids 2 to 54 of SEQ ID NO: 2 with or without a glutamine residue or a pyroglutamate attached to its N-terminus, and even more preferably it consists of the amino acid sequence shown as amino acids 2 to 54 of SEQ ID NO: 2.

Variant: When used herein, a "variant" of brazzein means a sweet protein which has a modified amino acid sequence as compared to the amino acid sequence of brazzein, i.e., an amino acid sequence wherein one or more (several) amino acids have been substituted, deleted and/or inserted.

Substantially pure sweet protein: The term "substantially pure sweet protein" denotes herein a sweet protein preparation that contains at most 20%, preferably at most 10%, more preferably at most 5%, more preferably at most 4%, more preferably at most 3%, even more preferably at most 2%, most preferably at most 1%, and even most preferably at most 0.5% by weight of other protein material with which it is natively or recombinantly associated. It is, therefore, preferred that the substantially pure sweet protein is at least 80% pure, preferably at least 90% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total protein material present in the preparation. The sweet proteins of the present invention are preferably in a substantially pure form, i.e., that the sweet protein preparation is essentially free of other protein material with which it is natively or recombinantly associated. This can be accomplished, for example, by purifying the sweet protein by classical purification methods.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch (1970) *J. Mol. Biol.* 48: 443-453) as implemented in the Needle program of the EMBOSS package (EMBOSS: The European Molecular Biology Open Software Suite, Rice et al. (2000) *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch (1970) supra) as implemented in the Needle program of the EMBOSS package (EMBOSS: The European Molecular Biology Open Software Suite, Rice et al. (2000), supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a polynucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, RNA, synthetic, or recombinant nucleotide sequence.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression from a polynucleotide encoding a sweet protein of the present invention. Each control sequence may be native or foreign to the nucleotide sequence encoding the sweet protein in nature or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a sweet protein.

Operably linked: The term "operably linked" denotes herein a configuration in which a control sequence is placed at an appropriate position relative to the coding sequence of the polynucleotide sequence such that the control sequence directs the expression from the coding sequence of a sweet protein according to the invention.

Expression: The term "expression" in the context of the present invention includes any step involved in the production of the sweet protein according to the invention including, but not limited to, transcription, post-transcriptional modification, translation, post-translational modification, and secretion.

Expression vector: The term "expression vector" is defined herein as a linear or circular DNA molecule that comprises a polynucleotide encoding a protein, such as a sweet protein of the present invention, and is operably linked to additional nucleotides that provide for its expression.

Host cell: The term "host cell", as used herein, refers to a cell that has been transformed, transfected, transduced, or the like, with a nucleic acid construct or expression vector comprising a polynucleotide encoding a sweet protein, and from which the sweet protein can be expressed according to a method of the present invention.

DETAILED DESCRIPTION OF THE INVENTION

A Method of Producing a Recombinant Sweet Protein

The present invention relates to a method of producing a recombinant sweet protein comprising an amino acid sequence having at least 70% identity to amino acids 2 to 54 of SEQ ID NO: 2.

In a preferred aspect, the recombinant sweet protein comprises an amino acid sequence having at least 75%, preferably at least 80%, more preferably at least 85%, even more preferably at least 90%, most preferably at least 95%, and even most preferably at least 96%, at least 97%, at least 98%, or at least 99%, identity to amino acids 2 to 54 of SEQ ID NO: 2. In a preferred aspect, the recombinant sweet protein has an amino acid sequence that differs by at most ten amino acids, preferably by at most five amino acids, more preferably by at most four amino acids, even more preferably by at most three amino acids, most preferably by at most two amino acids, and even most preferably by at most one amino acid from the amino acid sequence shown as amino acids 2 to 54 of SEQ ID NO: 2.

In a more preferred aspect, the recombinant sweet protein comprises the amino acid sequence of amino acids 2 to 54 of SEQ ID NO: 2. In a more preferred aspect, the recombinant sweet protein consists of the amino acid sequence shown as amino acids 2 to 54 of SEQ ID NO: 2 with or without a glutamine, glutamic acid or pyroglutamate residue attached to its N-terminus. In an even more preferred aspect, the recombinant sweet protein consists of the amino acid sequence shown as amino acids 2 to 54 of SEQ ID NO: 2 with or without a glutamine residue or a pyroglutamate attached to its N-terminus. In a most preferred aspect, the recombinant sweet protein consists of the amino acid sequence shown as amino acids 2 to 54 of SEQ ID NO: 2.

Amino acids 2 to 54 of SEQ ID NO: 2 is the amino acid sequence of one of the three natural forms of brazzein which can be obtained from the West African climbing plant *Pentadiplandra brazzeana* Baillon (WO9531547). A recombinant sweet protein produced by the method of the present invention may be brazzein or it may be another sweet protein comprising an amino acid sequence which is at least 70% identical to that of brazzein. Such other recombinantly produced sweet proteins having sequence similarity with brazzein may be obtainable from other plants, preferably from plants which are evolutionary close to *P. brazzeana*.

In a preferred aspect, the recombinant sweet protein is brazzein or a variant of brazzein.

A variant of brazzein comprises a substitution, deletion, and/or insertion of one or more (or several) amino acids as compared to the polypeptide sequence of brazzein comprising or consisting of amino acids 2 to 54 of SEQ ID NO: 2. The total number of amino acid substitutions, deletions and/or insertions as compared to the amino acid sequence shown as amino acids 2 to 54 of SEQ ID NO: 2 may be at most 10, preferably at most 9, more preferably at most 8, more preferably at most 7, more preferably at most 6, more preferably at most 5, more preferably at most 4, even more preferably at most 3, most preferably at most 2, and even most preferably 1.

In one aspect, such amino acid changes are of a minor nature, that is conservative amino acid substitutions or insertions that do not significantly affect the folding and/or functionality of the protein; small deletions, typically of one to about 5 amino acids; small amino- or carboxyl-terminal extensions, such as an amino-terminal methionine residue; a small linker peptide; or a small extension that facilitates purification by changing net charge or another function, such as a poly-histidine tag, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties are altered as compared to wild-type brazzein. For example, amino acid changes may improve the thermal stability of the protein, or the sweetness potency, the taste profile or the sweetness strength.

A variant of brazzein may, e.g., be one disclosed in WO 00/61759 or in WO 08/112,475.

The method of the present invention comprises cultivating an *Aspergillus* host cell comprising a nucleic acid construct comprising a polynucleotide encoding the sweet protein under conditions conducive for production of the sweet protein.

In a preferred aspect, the host cell is an *Aspergillus oryzae* host cell, an *Aspergillus niger* host cell, an *Aspergillus aculeatus* host cell, an *Aspergillus awamori* host cell, an *Aspergillus fumigates* host cell, an *Aspergillus foetidus* host cell, an *Aspergillus japonicas* host cell, or an *Aspergillus nidulans* host cell. In a more preferred aspect, the host cell is an *Aspergillus oryzae* host cell or an *Aspergillus niger* host cell. In an even more preferred aspect, the host cell is an *Aspergillus oryzae* host cell.

In another preferred aspect, the sweet protein is encoded with a propeptide in the N-terminus. A protein including a propeptide is generally immature and probably non-functional and can be converted to a mature functional protein by catalytic or autocatalytic cleaving off of the propeptide. In a more preferred aspect, the nucleic acid construct comprises the polynucleotide encoding the sweet protein operably linked to a nucleotide sequence encoding a propeptide comprising or consisting of an amino acid sequence having at least 70%, preferably at least 75%, more preferably at least 80%, more preferably at least 85%, even more preferably at least 90%, most preferably at least 95%, and even most preferably at least 96%, at least 97%, at least 98%, or at least 99%, identity to amino acids −32 to −1 of SEQ ID NO: 2. Preferably, the sweet protein is recovered according to step b) in a form where the propeptide has been cleaved off. More preferably, the propeptide is cleaved off by a protease expressed by the host cell.

In another preferred aspect, the sweet protein is encoded with a signal peptide in the N-terminus. Where both signal peptide and propeptide sequences are present at the N-terminus of a protein, the propeptide sequence is positioned next to the N-terminus of the mature protein and the signal peptide sequence is positioned next to the N-terminus of the propeptide sequence. The signal peptide is cleaved off by the host cell before the sweet protein is being recovered according to step b). Preferably, it is cleaved off by the host cell before, during or immediately after secretion. In a more preferred aspect, the nucleic acid construct comprises the polynucleotide encoding the sweet protein operably linked to a nucleotide sequence encoding a signal peptide comprising or consisting of an amino acid sequence having at least 70%, preferably at least 75%, more preferably at least 80%, more preferably at least 85%, even more preferably at least 90%, most preferably at least 95%, and even most preferably at least 96%, at least 97%, at least 98%, or at least 99%, identity to amino acids −55 to −33 of SEQ ID NO: 2.

In an even more preferred aspect, the nucleic acid construct comprises the polynucleotide encoding the sweet protein operably linked to a first nucleotide sequence encoding a signal peptide comprising or consisting of an amino acid sequence having at least 70%, preferably at least 75%, more preferably at least 80%, more preferably at least 85%, even more preferably at least 90%, most preferably at least 95%, and even most preferably at least 96%, at least 97%, at least 98%, or at least 99%, identity to amino acids −55 to −33 of SEQ ID NO: 2, and a second nucleotide sequence encoding a propeptide comprising or consisting of an amino acid sequence having at least 70%, preferably at least 75%, more preferably at least 80%, more preferably at least 85%, even more preferably at least 90%, most preferably at least 95%, and even most preferably at least 96%, at least 97%, at least 98%, or at least 99%, identity to amino acids −32 to −1 of SEQ ID NO: 2. Preferably, the sweet protein is recovered in a form where the signal peptide and the propeptide have been cleaved off.

In another preferred aspect, the nucleic acid construct comprises one or more intron sequence(s). Eukaryotic genes may be interrupted by intervening sequences (introns) which must be modified in precursor transcripts in order to produce functional mRNAs. This process of intron removal is known as pre-mRNA splicing. Usually, a branchpoint sequence of an intron is necessary for intron splicing through the formation of a lariat. Signals for splicing reside directly at the boundaries of the intron splice sites. The boundaries of intron splice sites usually have the consensus intron sequences GT and AG at their 5' and 3' extremities, respectively. While no 3' splice sites other than AG have been reported, there are reports of a few exceptions to the 5' GT splice site. For example, there are precedents where CT or GC is substituted for GT at the 5' boundary. There is also a strong preference for the nucleotide bases ANGT to follow GT where N is A, C, G, or T (primarily A or T in Saccharomyces species), but there is no marked preference for any particular nucleotides to precede the GT splice site. The 3' splice site AG is primarily preceded by a pyrimidine nucleotide base (Py), i.e., C or T.

The number of introns that can interrupt a fungal gene ranges from one to two, three, four, five, six, seven, eight, nine, ten, eleven, twelve or more introns. They may be distributed throughout a gene or situated towards the 5' or 3' end of a gene. In *Saccharomyces cerevisiae*, introns are located primarily at the 5' end of the gene. Introns may be generally less than 1 kb in size, and usually are less than 400 bp in size in yeast and less than 100 by in filamentous fungi.

The *Saccharomyces cerevisiae* intron branchpoint sequence 5'-TACTAAC-3' rarely appears exactly in filamentous fungal introns. Sequence stretches closely or loosely resembling TACTAAC are seen at equivalent points in filamentous fungal introns with a general consensus NRCTRAC where N is A, C, G, or T, and R is A or G. For example, the fourth position T is invariant in both the *Neurospora crassa* and *Aspergillus nidulans* putative consensus sequences. Furthermore, nucleotides G, A, and C predominate in over 80% of the positions 3, 6, and 7, respectively, although position 7 in *Aspergillus nidulans* is more flexible with only 65% C. However, positions 1, 2, 5, and 8 are much less strict in both *Neurospora crassa* and *Aspergillus nidulans*. Other filamentous fungi have similar branchpoint stretches at equivalent positions in their introns, but the sampling is too small to discern any definite trends.

In a more preferred aspect, the nucleic acid construct comprises the second intron from the *A. niger* glucoamylase gene. This intron may be inserted, e.g., in the signal peptide as described in Example 1. However, this and/or other introns may also be inserted at various other positions, e.g., distributed throughout the coding sequence or situated towards the 5' or 3' end of the construct.

In another more preferred aspect, the nucleic acid construct comprises an intron comprising or consisting of a nucleotide sequence having at least 70%, preferably at least 75%, more preferably at least 80%, more preferably at least 85%, even more preferably at least 90%, most preferably at least 95%, and even most preferably at least 96%, at least 97%, at least 98%, or at least 99%, identity to nucleotides 59 to 113 of SEQ ID NO: 1.

In a preferred aspect, the sweet protein is secreted from the host cell. In another preferred aspect, the sweet protein is secreted from the host cell in a functional form. In another preferred aspect, the sweet protein is secreted from the host cell in a soluble form. In another preferred aspect, the sweet protein is secreted from the host cell in a form where it has at least one, preferably at least two, more preferably at least three, and most preferably four, of its native disulfide bonds.

In the method of the present invention, the cells are cultivated in a nutrient medium suitable for production of the sweet protein using methods well known in the art. For example, the cells may be cultivated by shake flask cultivation, and small-scale or large-scale fermentation (including continuous, batch, fed-batch, or solid state fermentations) in laboratory or industrial fermentors performed in a suitable medium and under conditions allowing the sweet protein to be expressed and recovered. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The sweet protein is secreted into the nutrient medium and can be recovered directly here from.

The sweet protein may be recovered using methods known in the art. For example, the sweet protein may be recovered from the nutrient medium by conventional procedures including, but not limited to, centrifugation, filtration, extraction, spray-drying, evaporation, or precipitation.

In a preferred aspect, the sweet protein is recovered from the fermentation tank in a functional form. In another preferred aspect, the sweet protein is recovered from the fermentation tank in a soluble form. In another preferred aspect, the sweet protein is recovered from the fermentation tank in a form where it has at least one, preferably at least two, more preferably at least three, and most preferably four, of its native disulfide bonds.

The sweet protein obtained by the method of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., Protein Purification, J.-C. Janson and Lars Ryden, editors, VCH Publishers, New York, 1989) to obtain substantially pure sweet protein. In one aspect, the sweet protein may be purified by increasing the temperature to differentially precipitate other proteins. In a preferred aspect, the sweet protein is purified by filtration.

Polynucleotides

In another aspect, the present invention relates to an isolated polynucleotide comprising a nucleotide sequence having at least 70% identity to nucleotides 233 to 391 of SEQ ID NO: 1, which encodes a sweet protein.

In a preferred aspect, the isolated polynucleotide comprises a nucleotide sequence having at least 75%, preferably at least 80%, more preferably at least 85%, even more preferably at least 90%, most preferably at least 95%, and even most preferably at least 96%, at least 97%, at least 98%, or at least 99%, identity to nucleotides 233 to 391 of SEQ ID NO: 1. In a more preferred aspect, the isolated polynucleotide comprises the nucleotide sequence shown as nucleotides 233 to 391 of SEQ ID NO: 1.

The present invention also relates to polynucleotides comprising one or more alternative nucleotides or codons in the mature sweet protein coding sequence of SEQ ID NO: 1, in which the nucleotide sequence encodes a mature sweet protein having or comprising the amino acid sequence shown as amino acids 2 to 54 of SEQ ID NO: 2.

The present invention also relates to polynucleotides comprising one or more alternative nucleotides or codons in the mature sweet protein coding sequence of SEQ ID NO: 1, in which the nucleotide sequence encodes a variant of the mature sweet protein having or comprising the amino acid sequence shown as amino acids 2 to 54 of SEQ ID NO: 2. Modification of a nucleotide sequence encoding a sweet protein which can be produced by a method according to the present invention, such as modification of the mature sweet protein coding sequence of SEQ ID NO: 1, may result in the synthesis of sweet proteins substantially similar to brazzein. The term "substantially similar" to brazzein refers to non-naturally occurring forms of brazzein. These proteins may differ in some engineered way from brazzein as isolated from its native source, e.g., artificial variants that differ in thermal stability, sweetness potency, taste profile, sweetness strength, or the like. The variant polynucleotide sequence may be constructed on the basis of the nucleotide sequence presented as the mature sweet protein coding sequence of SEQ ID NO: 1, e.g., by introduction of nucleotide substitutions that give rise to a different amino acid sequence. For a general description of nucleotide substitution, see, e.g., Ford et al. (1991) *Protein Expression and Purification* 2: 95-107.

It will be apparent to those skilled in the art that such substitutions can be made outside the regions critical to the functionality of the protein and still result in a sweet protein. Amino acid residues essential to the functionality of the sweet protein encoded by an isolated polynucleotide of the invention, and therefore preferably not subject to substitution, may be identified according to procedures known in the art, such as site-directed mutagenesis or alanine-scanning mutagenesis. In the latter technique, mutations are introduced at every positively charged residue in the molecule, and the resultant mutant molecules are taste tested to identify amino acid residues that are critical to the functionality of the sweet protein. Sites of relevance for possible substitution can also be determined by analysis of the three-dimensional structure as determined by such techniques as nuclear magnetic resonance analysis, crystallography or photo affinity labelling.

Nucleic Acid Constructs

The present invention also relates to nucleic acid constructs comprising an isolated polynucleotide of the present invention operably linked to one or more (several) control sequences that direct the expression of the coding sequence in a suitable host cell, preferably in an *Aspergillus* host cell, under conditions compatible with the control sequences.

An isolated polynucleotide encoding a sweet protein which can be produced by a method according to the present invention may be manipulated in a variety of ways to provide for expression of the sweet protein. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell, preferably by an *Aspergillus* host cell, for expression of a polynucleotide encoding a sweet protein which can be produced according to a method of the present invention. The promoter sequence contains transcriptional control sequences that mediate the expression of the protein. The promoter may be any nucleotide sequence that shows transcriptional activity in the host cell including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell, such as an *Aspergillus* host cell, are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* betaglucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* betaxylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

The control sequence may also be a suitable transcription terminator sequence, a sequence recognized by a host cell, preferably by an *Aspergillus* host cell, to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, i.e., a nontranslated region of an mRNA that is important for translation by the host cell. The leader sequence is operably linked to the 5' terminus of the nucleotide sequence encoding the protein. Any leader sequence that is functional in the host cell may be used in the present invention.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, i.e., a sequence operably linked to the 3' terminus of the nucleotide sequence which, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding sequence that codes for an amino acid sequence linked to the N-terminus of the sweet protein and directs it into the cell's secretory pathway. In the context of the present invention, the 5' end of the coding sequence of the nucleotide sequence may contain a signal peptide coding sequence that directs it into the *Aspergillus* host cell's secretory pathway. The signal peptide coding sequence may be required as the coding sequence for brazzein does not naturally contain a signal peptide coding sequence.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

The control sequence may also be a propeptide coding sequence that codes for an amino acid sequence positioned at the N-terminus of the sweet protein. The propeptide coding sequence may be obtained from the genes for *Rhizomucor miehei* aspartic proteinase, and *Myceliophthora thermophila* laccase (WO 95/33836).

In a preferred aspect, the present invention relates to a nucleic acid construct comprising an isolated polynucleotide of the invention operably linked to one or both of a first nucleotide sequence encoding a signal peptide comprising or consisting of an amino acid sequence having at least 70%, preferably at least 75%, more preferably at least 80%, more preferably at least 85%, even more preferably at least 90%, most preferably at least 95%, and even most preferably at least 96%, at least 97%, at least 98%, or at least 99%, identity to amino acids −55 to −33 of SEQ ID NO: 2, and a second nucleotide sequence encoding a propeptide comprising or consisting of an amino acid sequence having at least 70%, preferably at least 75%, more preferably at least 80%, more preferably at least 85%, even more preferably at least 90%, most preferably at least 95%, and even most preferably at least 96%, at least 97%, at least 98%, or at least 99%, identity to amino acids −32 to −1 of SEQ ID NO: 2.

In a more preferred aspect, the present invention relates to a nucleic acid construct comprising an isolated polynucleotide of the invention operably linked to one or both of a first nucleotide sequence encoding a signal peptide comprising or consisting of the amino acid sequence show as amino acids −55 to −33 of SEQ ID NO: 2, and a second nucleotide sequence encoding a propeptide comprising or consisting of the amino acid sequence shown as amino acids −32 to −1 of SEQ ID NO: 2.

Preferably, the first nucleotide sequence comprises or consists of nucleotides 10 to 58 combined with nucleotides 114 to 133 of SEQ ID NO: 1. Preferably, the second nucleotide sequence comprises or consists of nucleotides 134 to 229 of SEQ ID NO: 1.

In a preferred aspect, the nucleic acid construct of the invention contains 1, 2, 3, 4, or 5 intron sequence(s), preferably 1, 2, 3 or 4 intron sequence(s), more preferably 1, 2 or 3 intron sequence(s), even more preferably 1 or 2 intron sequence(s), and most preferably one intron sequence.

In another preferred aspect, the nucleic acid construct of the invention comprises a nucleic acid sequence encoding a sweet protein and at least one, preferably at least two, more preferably at least three, and most preferably at least four intron sequences.

The intron sequence(s) may be located in the signal-, pro- or mature peptide encoding part of the nucleic acid construct of the invention. When the nucleic acid construct contains more than one intron, the introns can be located in different parts of the construct. The intron sequence(s) may in fact be located in any part of the gene encoding the sweet protein which is transcribed into mRNA.

In a preferred aspect, the present invention relates to a nucleic acid construct comprising a polynucleotide sequence encoding a sweet protein which is operably linked to a polynucleotide sequence encoding a signal peptide and a propeptide and which comprises an intron, wherein such nucleic acid construct comprises a nucleotide sequence having at least 70%, preferably at least 75%, more preferably at least 80%, more preferably at least 85%, even more preferably at least 90%, most preferably at least 95%, and even most preferably at least 96%, at least 97%, at least 98%, or at least 99%, identity to nucleotides 10 to 391 of SEQ ID NO: 1.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding a sweet protein at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The vector to be used according to the present invention has to be compatible with the host cell, preferably the *Aspergillus* host cell, into which the vector is to be introduced. The vector may be a linear or closed circular plasmid.

The vector may be an autonomously replicating vector, i.e., a vector that exists as an extra-chromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For autonomous replication, the vector may further comprise an origin of replication enabling the vector to replicate autonomously in the host cell. The origin of replication may be any plasmid replicator mediating autonomous replication that functions in the cell. The term "origin of replication" or "plasmid replicator" is defined herein as a nucleotide sequence that enables a plasmid or vector to replicate in vivo.

Examples of origins of replication useful in a filamentous fungal cell are AMA1 and ANS1 (Gems et al. (1991) *Gene* 98: 61-67; Cullen et al. (1987) *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art.

Host Cells

The present invention also relates to recombinant *Aspergillus* host cells, comprising an isolated polynucleotide of the present invention, which are to be used in the recombinant production of the sweet protein. A vector comprising a polynucleotide of the present invention is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication.

Suitable procedures for transformation of *Aspergillus* host cells are described in EP 238 023 and Yelton et al. (1984) *Proceedings of the National Academy of Sciences USA* 81: 1470-1474.

Method of Producing a Sweetening Agent

As mentioned above, one advantage of producing a sweet protein according to a method of the present invention is that the protein is obtained in a fully functional form, and following appropriate purification, it can be directly applied as a sweetening agent. In a preferred aspect, the invention therefore relates to a method of producing a sweetening agent, which comprises:
a) cultivating an *Aspergillus* host cell comprising a polynucleotide sequence encoding a sweet protein comprising an amino acid sequence having at least 70% identity to amino acids 2 to 54 of SEQ ID NO: 2 under conditions conducive for production of the sweet protein;
b) recovering the sweet protein in a functional form as secreted from the host cell; and
c) applying the functional sweet protein as active ingredient in the sweetening agent.

In another preferred aspect, the present invention relates to method of producing a sweetening agent, which comprises:
a) cultivating an *Aspergillus* host cell comprising a polynucleotide sequence encoding a sweet protein comprising an amino acid sequence having at least 70% identity to amino acids 2 to 54 of SEQ ID NO: 2 under conditions conducive for production of the sweet protein;
b) recovering the sweet protein essentially in its oxidized form and maintaining it essentially oxidized; and
c) applying the essentially oxidized sweet protein as active ingredient in the sweetening agent.

The sweet protein is recovered essentially in its oxidized form and maintained essentially oxidized. This means that the sweet protein as applied in the sweetening agent has not been denatured by addition of reducing agent followed by oxidation. I.e., the sweet protein is applied in the sweetening agent essentially in the 3-dimensional form it was folded into when secreted from the host cell.

Preferably, in a method of producing a sweetening agent according to the present invention, the sweet protein comprises an amino acid sequence having at least 75%, preferably at least 80%, more preferably at least 85%, even more preferably at least 90%, most preferably at least 95%, and even most preferably at least 96%, at least 97%, at least 98%, or at least 99%, identity to amino acids 2 to 54 of SEQ ID NO: 2.

In another preferred aspect, the sweet protein has an amino acid sequence that differs by at most ten amino acids, preferably by at most five amino acids, more preferably by at most four amino acids, even more preferably by at most three amino acids, most preferably by at most two amino acids, and even most preferably by at most one amino acid from the sequence shown as amino acids 2 to 54 of SEQ ID NO: 2.

In a more preferred aspect, the sweet protein comprises the amino acid sequence shown as amino acids 2 to 54 of SEQ ID NO: 2. In an even more preferred aspect, the sweet protein consists of the amino acid sequence shown as amino acids 2 to 54 of SEQ ID NO: 2.

In a preferred aspect, the sweet protein is brazzein or a variant of brazzein. In a more preferred aspect, the sweet protein is brazzein.

Uses

The present invention is also directed to methods for using the sweet protein obtained by a method of the invention for sweetening of food, beverage and/or medication products for human consumption.

A sweet protein obtained by a method of the invention may be utilized for any application where a low-calorie sweetener is desired. Typical applications include baked goods such as breads, cookies, cakes, brownies, etc.; beverages such as coffee, tea and soft drinks; confectionaries such as chocolates and candies; chewing gum; dairy products such as cheesecake, ice cream, smoothies, yoghurt, yoghurt drink, drinking chocolate, cocoa drinks, etc.; cereal bars, health bars, protein bars; tablet coatings; etc.

A sweet protein obtained by a method of the invention may be blended with other sweeteners, e.g., with aspartame, to complement the flavour of such other sweetener(s).

The present invention thus in one aspect relates to a method of increasing the sweetness of a food, beverage or medication product for human consumption comprising the step of adding a sufficient amount of a sweet protein to the product, so that the product has an increased sweetness, wherein the sweet protein has been produced according to a method as described herein.

In another aspect, the invention relates to a food, beverage or medication product for human consumption which comprises a sweet protein which has been produced according to a method as described herein.

EXAMPLES

Example 1

Recombinant Expression of Brazzein in Filamentous Fungus *Aspergillus oryzae*

The protein sequence of wild type brazzein from *Pentadiplandra brazzeana* Baillon was acquired from the article by Ming D, Hellekant G (1994) "Brazzein, a new high-potency thermostable sweet protein from *Pentadiplandra brazzeana* B" *FEBS Lett.* 355(1): 106-108. A synthetic gene was designed from the brazzein protein sequence using a codon usage table, which has been made based on the highly expressed amg genes from *Aspergillus oryzae*. DNA primers covering the whole brazzein coding sequence of SEQ ID NO: 1 were made, and the gene was pieced together using Splicing by Overlapping Extension PCR. In the process, the N-terminal glutamine was changed to a glutamic acid. To facilitate secretion of the brazzein molecule, a signal peptide from the Plectasin molecule from *Pseudoplectania nigrella* was added at the N-terminus. Moreover, we have added the propeptide from Plectasin at the N-terminus to facilitate expression. To increase expression, we have inserted the second intron from the *A. niger* glucoamylase gene in the plectasin signal peptide at codon 17 as described in example 3 in WO 06/097464. The open reading frame has been flanked with a BamHI restriction site and a kozak sequence in the 5'-end and an XhoI restriction site in the 3'-end.

The nucleotide sequence encoding the whole open reading frame including the intron can be found in SEQ ID NO: 1.

The amino acid sequence of the open reading frame including the signal peptide and the pro peptide can be found in SEQ ID NO: 2.

The plasmid pCOIs703 is a derivative of pJaL721 (Example 17, WO 03/008575), where a gene fragment of 1489 bp has been inserted in the BamHI and XhoI sites as a stuffer for removal when inserting fragments in the BamHI and XhoI sites. Moreover, the promoter governing expression of the ura3 gene for selection in *E. coli* has been exchanged with a stronger promoter.

A DNA molecule encoding SEQ ID NO: 1 was cut with BamHI and XhoI. The linear DNA fragment was ligated in pCOIs703 cut with BamHI/XhoI. The insert was sequenced and verified to be identical to the original sequence. The resulting plasmid was named pCOIs781.

Plasmid pCOIs781 was transformed in *A. oryzae* BECh2 using amdS selection, selecting for growth on acetamide as previously described in WO 03/044049. Twenty transformants were reisolated twice and grown in YPM (1% yeast extract, 2% bacto peptone and 2% maltose) for four days at 30° C. Expression levels were evaluated by analysing supernatants by SDS PAGE essentially as described in WO 03/044049. The best transformants were selected for tank fermentation in ten liter scale. The yield from the tank fermentation is expected to be industrially relevant.

Example 2

Brazzein Purification

Fermentation broth from Example 1 was filtered through a 0.22 μm filter. Ammonium sulphate was added to the permeate to a final conc. of 2 M and applied on a butyl-Sepharose column. Brazzein was eluted with a gradient with decreasing ammonium conc. and fractions containing brazzein was pooled. The brazzein pool was filtered through a 30 kDa filter and the permeate was concentrated using a 3 kDa filter. The protein conc. of this brazzein batch was estimated to be 1.5 mg/ml.

Example 3

Sensory Evaluation of the Sweetness of Brazzein Produced in *A. oryzae*

A test taste panel of six persons was used to evaluate the brazzein sweetness compared to sucrose. The brazzein batch from Example 2 was diluted 30 fold to a final conc. of 50 mg/l with 20% skim milk in order to avoid adsorption on surfaces. The sweetness was estimated using a standard of 0%, 0.68%, 1.37%, 2.74%, 5.48%, 11.0%, 21.9% (w/v) sucrose diluted in 20% (v/v) skim milk. The sweetness of this 50 mg/l brazzein dilution corresponded to an average sweetness of 2.57% (w/v) sucrose±0.55% sucrose (SD). Thus, the brazzein batch is 510 times sweeter than sucrose on weight basis at the present condition. The sweet taste delay of the brazzein was estimated to be 1.5 sec±1.2 sec (SD).

SD=standard deviation.

Example 4 pH Profile of the Sweet Taste of Brazzein Produced in *A. oryzae*

A taste panel of three persons estimated the pH profile of the sweet taste of brazzein compared to sucrose. 5 g/l whey protein (Lacprodan DI-9224, Arla Foods Ingredients) with 0%, 2%, 4%, 6%, 8%, 10%, 12%, 14% and 16% sucrose or 75 mg/l brazzein was adjusted with $H_3PO_4$, $Na_2HPO_4$ or NaOH to a final pH of 2.0, 3.9, 4.0, 5.0, 7.0 and 9.0. The sucrose equivalent sweet taste of 75 mg/l Brazzein is shown in Table 1.

TABLE 1

| pH | % sucrose | SD |
|---|---|---|
| 2.0 | 6.0 | 3.5 |
| 3.0 | 6.0 | 0.0 |
| 4.0 | 4.3 | 0.6 |
| 5.0 | 6.3 | 0.6 |
| 7.0 | 5.0 | 1.0 |
| 9.0 | 2.7 | 1.2 |

Example 5

Sucrose Replacement in Yoghurt Drinks

A test taste panel of three persons was made to evaluate brazzein sweetness in yoghurt drink. The yoghurt product Cheasy A38 (Arla Foods), which contains 0.1% milk fat, 4.3% milk protein, was diluted to a final conc. of 1% milk protein, with sucrose or a solution of brazzein produced in *A. oryzae*. Using a standard row of 0%, 2%, 4%, 6%, 8%, 10%, 12%, 14% and 16% sucrose with 23% Cheasy A38, it was found that the sweetness of 75 mg/l brazzein in 23% Cheasy A38 corresponds to an average of 7% sucrose±1% (SD) in 23% Cheasy A38. Thus, at the present condition in 23% Cheasy A38, the brazzein batch is 930 times sweeter than sucrose on weight basis.

Furthermore, the sweetness of brazzein and sucrose were additive as 6% sucrose+75 mg/l brazzein, taste like 12.7%±0.6% (SD) sucrose in 23% Cheasy A38. The presence of 6% sucrose almost removed the "sweet-taste delay sensation" from brazzein.

The invention claimed is:

1. A method of producing a recombinant sweet protein comprising an amino acid sequence having at least 90% identity to amino acids 2 to 54 of SEQ ID NO: 2, which comprises:
   a) cultivating an *Aspergillus* host cell comprising a nucleic acid construct comprising a polynucleotide encoding the sweet protein under conditions conducive for production of the sweet protein; and
   b) recovering the sweet protein
   wherein the sweet protein is secreted from the host cell in a functional form.

2. A method according to claim 1, wherein the sweet protein is brazzein or a variant of brazzein.

3. A method according to claim 1, wherein the host cell is an *Aspergillus oryzae* host cell or an *Aspergillus niger* host cell.

4. A method according to claim 1, wherein the nucleic acid construct comprises the polynucleotide encoding the sweet protein operably linked to a first nucleotide sequence encoding a signal peptide comprising or consisting of an amino acid sequence having at least 90% identity to amino acids -55 to -33 of SEQ ID NO: 2, and a second nucleotide sequence encoding a propeptide comprising or consisting of an amino acid sequence having at least 90% identity to amino acids -32 to -1 of SEQ ID NO: 2.

5. A method according to claim 4, wherein the sweet protein is recovered in a form where the signal peptide and the propeptide have been cleaved off.

6. A method according to claim 1, wherein the nucleic acid construct comprises one or more intron sequence(s).

7. The method of claim 1, wherein the recombinant sweet protein comprises an amino acid sequence having at least 95% identity to amino acids 2 to 54 of SEQ ID NO: 2.

8. The method of claim 1, wherein the recombinant sweet protein comprises an amino acid sequence having at least 97% identity to amino acids 2 to 54 of SEQ ID NO: 2.

9. The method of claim 1, wherein the recombinant sweet protein comprises an amino acid sequence having at least 98% identity to amino acids 2 to 54 of SEQ ID NO: 2.

10. The method of claim 1, wherein the recombinant sweet protein comprises an amino acid sequence having at least 99% identity to amino acids 2 to 54 of SEQ ID NO: 2.

11. The method of claim 1, wherein the recombinant sweet protein comprises the amino acid sequence shown as amino acids 2 to 54 of SEQ ID NO: 2.

12. The method of claim 1, wherein the recombinant sweet protein consists of the amino acid sequence shown as amino acids 2 to 54 of SEQ ID NO: 2.

13. A method of increasing the sweetness of a food, beverage or medication product for human consumption comprising the step of adding a sufficient amount of a sweet protein to the product, so that the product has an increased sweetness, wherein the sweet protein has been produced according to the method of claim 1.

14. A food, beverage or medication product for human consumption which comprises a sweet protein which has been produced according to the method of claim 1.

* * * * *